United States Patent [19]

Joffe

[11] Patent Number: 5,007,830
[45] Date of Patent: Apr. 16, 1991

[54] DEVICE FOR DETERMINING THE OCCLUSAL PLANE

[76] Inventor: Eugene Joffe, 79-10 34th Ave., Jackson Hts., N.Y. 11372

[21] Appl. No.: 362,268

[22] Filed: Jun. 6, 1989

[51] Int. Cl.⁵ .......................................... A61C 19/04
[52] U.S. Cl. ...................................... 433/68; 433/71
[58] Field of Search ............................ 433/68, 69, 71

[56] References Cited

U.S. PATENT DOCUMENTS 1,589,973  6/1926  Landa ..................................... 433/68

FOREIGN PATENT DOCUMENTS 3540756  5/1987  Fed. Rep. of Germany ........ 433/68
0745516  7/1980  U.S.S.R. ................................ 433/68

Primary Examiner—John J. Wilson
Attorney, Agent, or Firm—Ilya Zborovsky

[57] ABSTRACT

A device for determining an occlusal plane for making dental prostheses includes two horizontally pivotable members arranged to be brought in alignment with an ear-nose plane, and a further member vertically displaceable relative to the first mentioned members parallel to the latter to be brought in contact with plastic material on a base applied to an occlusal surface of remaining teeth or its equivalent.

7 Claims, 2 Drawing Sheets

DEVICE FOR DETERMINING THE OCCLUSAL PLANE

BACKGROUND OF THE INVENTION

The present invention relates to a device for determining an occlusal plane for teeth positioning for dental prostheses.

The determination of the occlusal plane of a patient for subsequent making of a dental prosthesis is a complicated process which involves placing into a patient's mouth a base plate with a plastic material so as to rest on remaining front teeth of an upper jaw or to be visually aligned with a lip line. The occlusal surface is then determined visually by operator. There are no devices which can insure an objective, completely accurate, and simple determination of the occlusal plane. It is believed that such devices would be highly desirable since they would significantly shorten the process of determination and increase its accuracy.

SUMMARY OF THE INVENTION

Accordingly, it is an object of the present invention to provide a device for determining an occlusal plane for teeth alignment, which has a simple construction, is easy to operate and provides for high accuracy of measurements.

In keeping with these features and with others which will become apparent hereinafter, one feature of the present invention resides, briefly stated, in a device which has two first pivotable members which pivot in a first plane about vertical axes, and a second member which is vertically displaceable parallel to the first members, so that the first members can be aligned with an ear-nose line, while the second member can be brought in contact with a plastic material on a base plate positioned on remaining teeth or their equivalent.

When the device is designed in accordance with these features, it attains the above specified objects and advantages.

The novel features of the present invention are set forth in particular in the appended claims. The invention itself however will be best understood from the following description of preferred embodiments which is accompanied by the following drawings.

DESCRIPTION OF PREFERRED EMBODIMENTS

Figure 1:
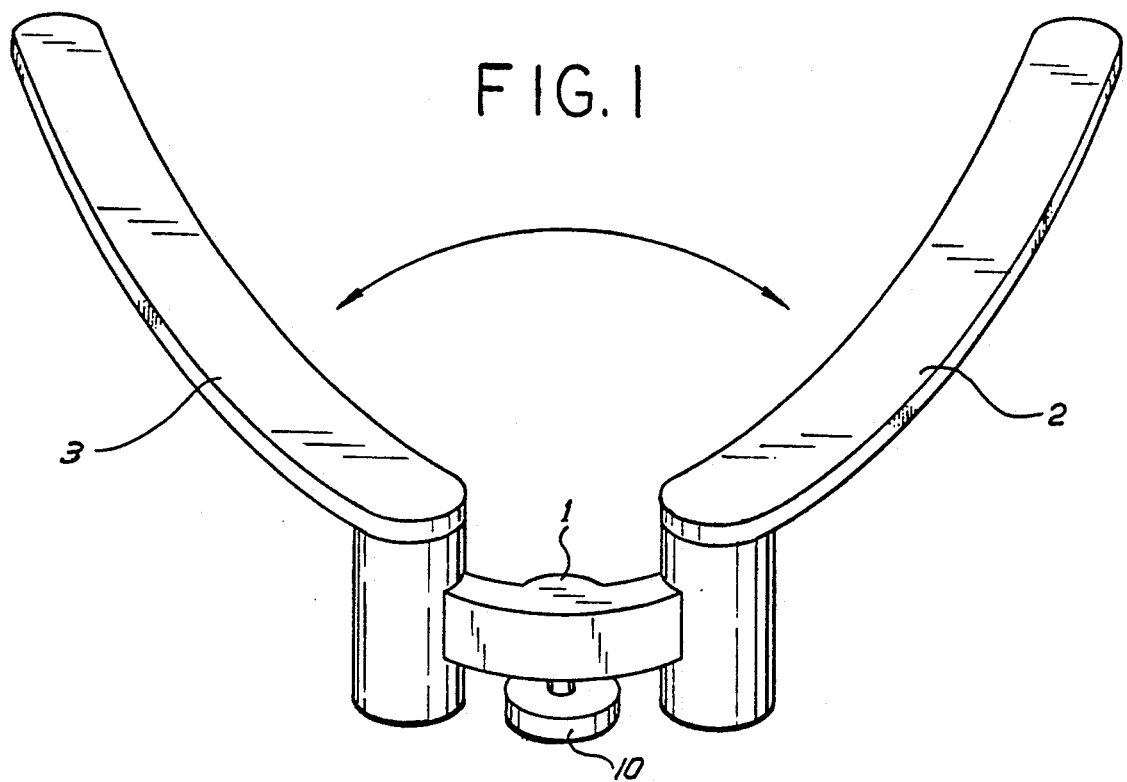
FIG. 1 is a perspective view of a part of an inventive device for determining an occlusal plane, showing two first members with a holding body and an adjusting member.

As can be seen from FIG. 1, a device for determining an occlusal plane has a holding body identified with reference numeral 1. Two first members 2 and 3 are pivotably mounted on the holding body 1. More particularly, one end of each first member is provided with a pin 4 which is received in a respective opening 5 of the holding body. Thereby the members 2 and 3 are turnable about vertical axes.

A second member 6 is provided with two pins 7 which are slidingly movable vertically in openings 8 provided in the holding body 1 and preferably coaxial with the opening 5. There is a certain amount of friction between the outer surfaces of the pins 7 and the walls of the openings 8, so that normally the pins 7 are firmly held in the openings and the second member is somewhat arrested in its position under the action of friction.

A central threaded opening 9 is formed in the holding body 1 centrally of the latter. An adjusting knob 10 is provided with a threaded pin 11 which engages with the threaded opening 9. A dentist can turn the adjusting knob 10 and displace the latter vertically relative to the holding body. An opposite side of the adjusting knob is provided with an abutting surface 12 facing downwardly therefrom, as can be seen from FIG. 3.

Figure 2:
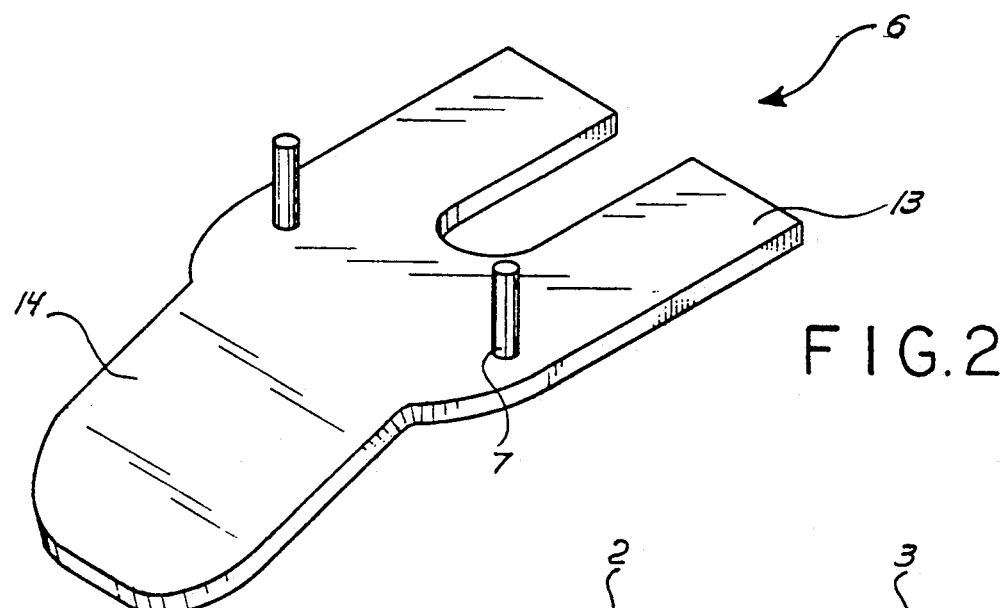
FIG. 2 is a perspective view of another part of the inventive device, showing a second member with a handle.

The second member 6 is preferably horseshoe-shaped and has two spaced legs 13. The device is provided with a handle 14 which can be formed integrally of one piece with the second member. The handle 14 is bent somewhat downwardly from the plane of the member 6, as can be seen from FIG. 2.

Figure 5:
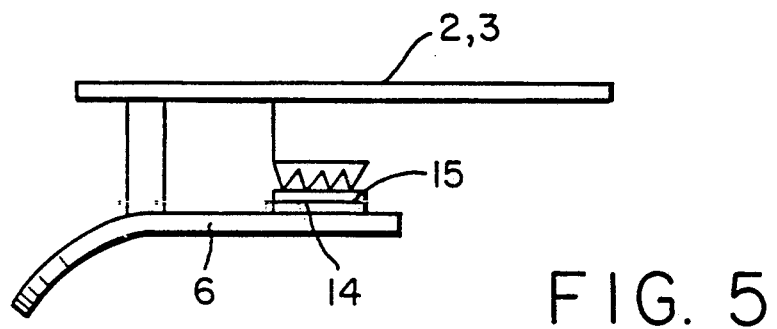
FIG. 5 is a view which schematically shows the operation of the inventive device.

The device operates in the following manner:

A dentist arranges the device so that the first members 2 and 3 surround the face of a patient. Then he turns the first members inwardly as close as possible. The first members are oriented by the dentist so that a plane of the first members coincides with an imaginary plane extending through the patient's nose base and ears lobes. After this, the knob 10 is turned by the dentist so that the surface 12 displaces the second member 6 away of the first members 2 and 3. This displacement is continued till the second member 6 can be inserted into the patient's mouth. Then the knob 10 is turned in an opposite direction to be withdrawn from the second member 6, and the latter is pushed up by the dentist so that the second member abuts from below against a plastic layer (wax, acrylic, etc) 14 applied on a base 15. Before the procedure the horseshoe base 15 is placed onto the occlusal surface of remaining front teeth or oriented in other ways, for example relative to a lip line of the patient. The second member 6 is always displaced parallel to the first members 2,3. In its above mentioned final position, it determines the desired occlusal surface of teeth alignment and impresses the same in the plastic materials, as shown in FIG. 5.

Figure 3:
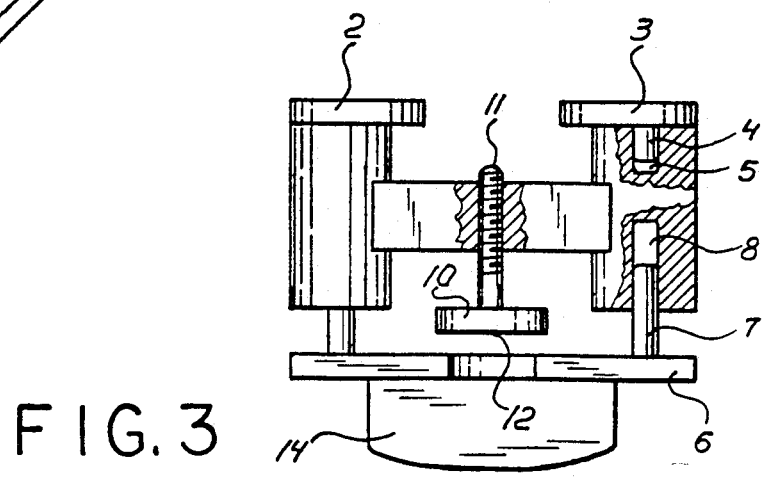
FIGS. 3 and 4 are a rear view and a side view of the inventive device.
Figure 4:
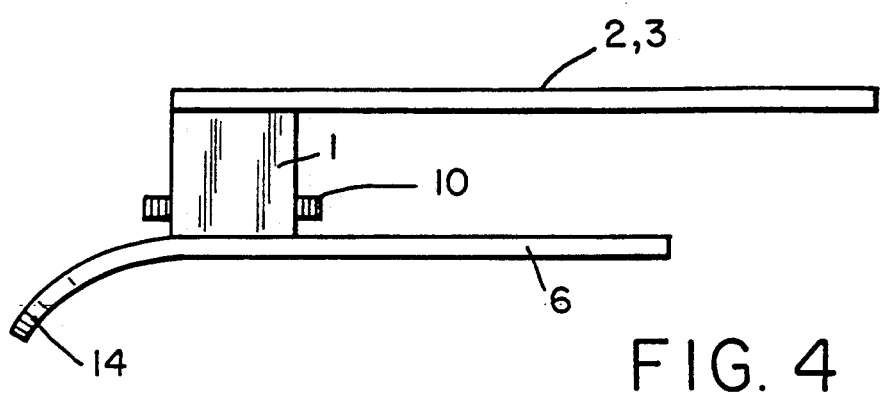
Figure 6:
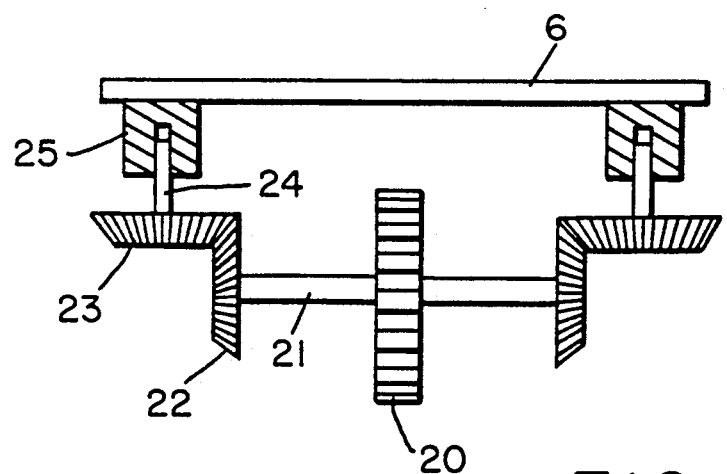
FIG. 6 is a view showing another modification of the adjusting member of the invention device.

FIG. 6 illustrates another embodiment of the adjusting knob. The knob 10 in FIG. 3 is to be displaced by horizontal turning about a vertical axis, which is inconvenient and causes undesirable horizontal shaking of the device. In the device of FIG. 6 the knob 20 also displaces the second member 6 in a vertical direction. However, for this purpose it is turnable by vertical movements about a horizontal axis. The knob 20 is seated on a shaft 21 which carries two bevel gears 22. The gears 22 are in engagement with further bevel gears 23 whose shafts 24 have threaded ends engaging in threaded openings of bushes 25 attached to the second member 6. In addition to the convenience of turning of the knob 20, another advantage of the construction of the knob unit of FIG. 6 is that the movements of the second member 6 in both opposite directions are performed positively by the drive, as opposed to manual pushing of the second member 6 upwardly in the first embodiment.

The invention is not limited to the details shown since various modifications and structural changes are possible without departing in any way from the spirit of the invention.

What is desired to be protected by Letters Patent is set forth in the appended claims.

I claim:

1. A device for determining an acclusal plane for teeth positioning in detal prostheses, comprising two first members pivotable about vertical axes in a first plane which can be aligned with an ear-nose plane of a patient;

a second member vertically adjustable relative to said first members and therefore said first plane so as to be brought in contact with plastic material on a base plate placed on an occlusal surface of remaining teeth or placed in correspondence with a lip line, said second member being movable parallel to said first members so that upon said contact said second member determines a position of a required occlusal surface;

means for moving said second member relative to said first members and including an adjusting element manually movable by a user;

a holding body, said first members being arranged pivotally relative to said holding body, said second member being arranged vertically displaceable relative to said holding body and having two pins;

two pivot pins each defining a respective one of said axes of pivoting of said first members, said holding body having two guiding openings in which said pins of said second member are vertically movably, said holding body further having two further guiding openings in which said pivot pins are turnably received, said first mentioned guiding openings being coaxial with said second mentioned guiding openings.

2. A device as defined in claim 1; and further comprising a handle arranged to be gripped by a user so as to hold the device.

3. A device as defined in claim 2, wherein said handle is connected with said second member.

4. A device as defined in claim 1, wherein said second member has a horseshoe shape.

5. A device as defined in claim 1, wherein said adjusting element is formed as a turnable knob arranged to turn and as a result of said turning to push said second member vertically relative to said first member.

6. A device as defined in claim 5, wherein said turnable knob is turnable about a vertical axis so as to move vertically, and to push said second member vertically.

7. A device as defined in claim 5, wherein said turnable knob is turnable about a horizontal axis so as to move said second member vertically.

* * * * *